(12) United States Patent
Sebban

(10) Patent No.: US 8,100,886 B2
(45) Date of Patent: *Jan. 24, 2012

(54) ASPIRATOR ASSEMBLY

(75) Inventor: Eric Sebban, Hollywood, FL (US)

(73) Assignee: Visiomed Group SA, Paris (FR)

( * ) Notice: Subject to any disclaimer, the term of this patent is extended or adjusted under 35 U.S.C. 154(b) by 247 days.

This patent is subject to a terminal disclaimer.

(21) Appl. No.: 11/978,015

(22) Filed: Aug. 15, 2007

(65) Prior Publication Data
US 2009/0048581 A1 Feb. 19, 2009

(51) Int. Cl.
*A61M 1/00* (2006.01)
(52) U.S. Cl. ........................... 604/540; 604/319
(58) Field of Classification Search .......... 604/19, 604/35, 319, 540, 73, 313–315, 317; 600/474, 600/549; 374/121, 158; 606/162
See application file for complete search history.

(56) References Cited

U.S. PATENT DOCUMENTS

| | | | |
|---|---|---|---|
| 4,797,840 A | 1/1989 | Fraden | |
| 5,167,235 A | 12/1992 | Seacord et al. | |
| 5,178,464 A | 1/1993 | Fraden | |
| 5,487,607 A | 1/1996 | Makita et al. | |
| 5,522,662 A | 6/1996 | Shiokawa | |
| 5,991,652 A | 11/1999 | Barthelemy et al. | |
| D436,173 S | 1/2001 | Hemon | |
| 6,196,714 B1 | 3/2001 | Bellifemine et al. | |
| D451,597 S | 12/2001 | Suh | |
| 6,471,679 B1 * | 10/2002 | Suh | 604/319 |
| 6,485,433 B1 | 11/2002 | Peng | |
| 6,517,511 B2 | 2/2003 | Yao | |
| 6,527,439 B1 | 3/2003 | Bellifemine | |
| 6,742,927 B2 | 6/2004 | Bellifemine | |
| 6,751,497 B2 | 6/2004 | Fraden | |
| D493,733 S | 8/2004 | Chen | |
| D494,672 S | 8/2004 | Wang | |
| 6,789,936 B1 | 9/2004 | Kraus et al. | |
| 7,001,066 B1 | 2/2006 | Bellifemine | |
| 7,048,437 B2 | 5/2006 | Bellifemine | |
| 7,093,974 B2 | 8/2006 | Kienitz | |
| 7,108,419 B2 | 9/2006 | Harr | |
| D535,746 S | 1/2007 | Grove et al. | |
| D549,114 S | 8/2007 | Sebban | |
| D583,263 S | 12/2008 | Sebban | |
| 2009/0076441 A1 * | 3/2009 | Sebban | 604/35 |

* cited by examiner

*Primary Examiner* — Tatyana Zalukaeva
*Assistant Examiner* — Benedict L Hanrahan
(74) *Attorney, Agent, or Firm* — Malloy & Malloy, P.A.

(57) ABSTRACT

An assembly structured to aspirate nasal cavity of individuals including, but not limited to, children. A hand held and hand operative casing includes a negative pressure source preferably battery operated, and a cover assembly removably connected to the casing and structured to at least partially define a receiving chamber. An inlet assembly is formed in the casing and communicates with the negative pressure source at least partially by means of a path of fluid flow. A container is removably disposed within the receiving chamber in a predetermined, operative orientation sufficient to receive and collect a predetermined portion or phase of the aspirated fluid, such as mucus is removed from the nasal cavity. The path of fluid flow is disposed, dimensioned and structured to restrict passage of the heavier, predetermined portion or phase of the aspirated fluid thereby facilitating its collection within the container, which is disposable along with the collected aspirated fluid after use.

17 Claims, 4 Drawing Sheets

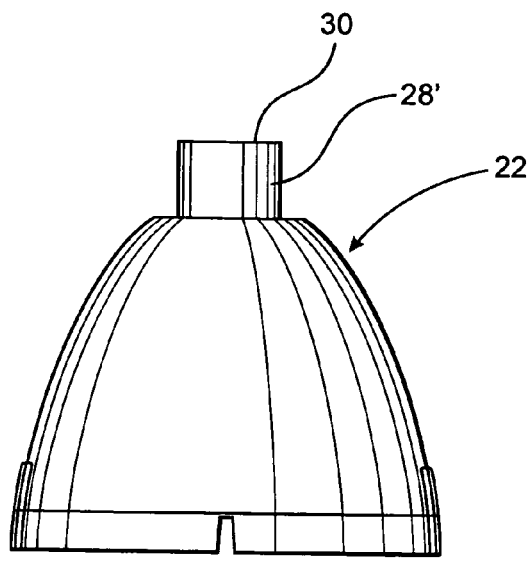
FIG. 6
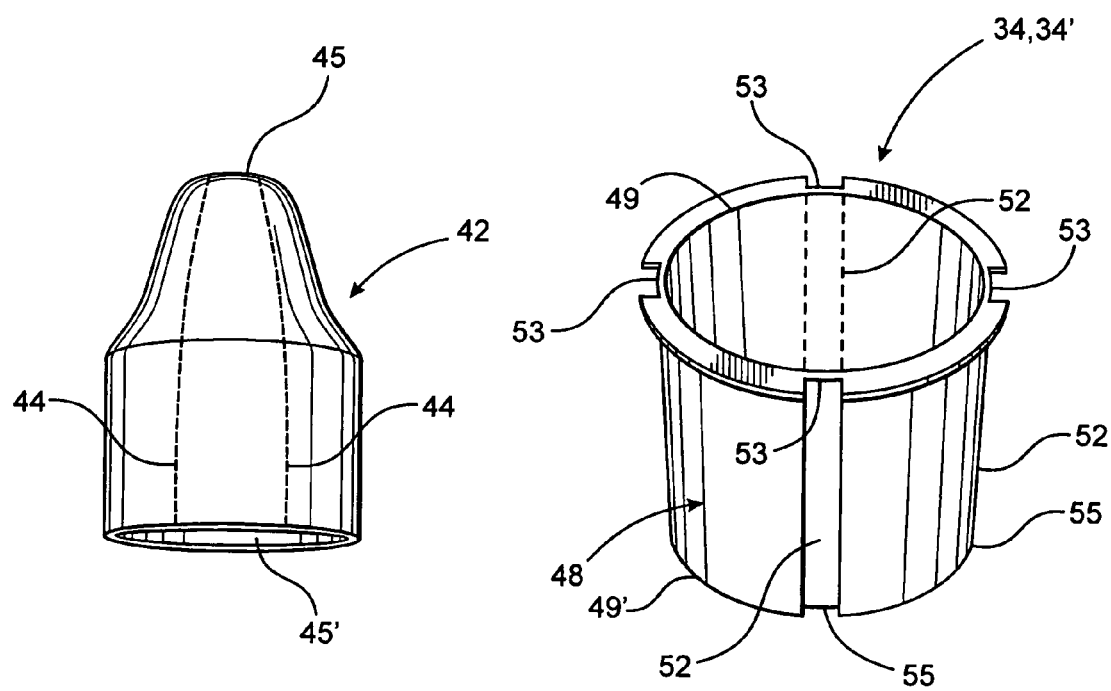
FIG. 7
FIG. 8

ASPIRATOR ASSEMBLY

BACKGROUND OF THE INVENTION

1. Field of the Invention

This invention relates to a hand held aspirating assembly structured to aspirate fluid from the nasal cavity of individuals specifically including, but not limited to, infants and children. A source of negative pressure is battery powered and a receiving chamber is cooperatively structured to house a removable collection container. A predetermined portion of the aspirated fluid, such as mucus, is collected in the container and collectively disposed therewith after the aspiration procedure has been completed.

2. Description of the Related Art

The ordinary cold, as well as more serious respiratory infections, can result in the blockage of the nasal passage or cavity due to the accumulation of mucus therein. In the case of adult individuals the collected mucus can frequently or at least partially be removed by forced expulsion when the individual blows his or her nose. However, in the case of small children or infants the self induced expulsion of the mucus by blowing ones nose typically has not been learned. Accordingly, in many instances fluid, and in particularly the mucus, built up in the nasal cavity or passage must be removed by other means. Removal of the mucus is also important for the general health of the individual at least to the extent of preventing or minimizing the drainage of the mucus back into the throat, lungs. In addition, inordinate collection of certain fluids in the nasal passage or cavities significantly increases the possibility of infection.

In cases involving infants and small children as well as adult individuals not capable of the self expulsion of mucus and other collections from the nasal cavity, an aspiration procedure is commonly applied. Conventionally known aspiration procedures are frequently accomplished by using a hand manipulated device such as a flexible or elastic material "squeeze" bulb connected to or otherwise directly associated with a nozzle structure or other appropriate applicator structured to be received within the nasal passage of an individual. With the interior of the squeeze bulb disposed in fluid communication with the nozzle, it is disposed to at least partially enter the nasal cavity or passage so as to be positioned in communicating relation with the mucus and/or other collected fluid therein. By virtue of the elastic or flexible nature of the material from which the squeeze bulb is formed, it can be manually collapsed, by the application of squeezing force thereon, and subsequently released. Such manipulation results in an at least partial vacuum or negative pressure being exerted on the collected fluids within the nasal cavity.

While such procedures and accompanying apparatus have been known for many years, it is commonly recognized that problems and disadvantages are associated with the application thereof. More specifically, because the negative pressure generated by the squeeze bulb is frequently insufficient, mucus and other fluids are not effectively removed from the nasal passage. Also, because of the inadequacy of the negative pressure developed, it is frequently required that the nozzle portion of the squeeze bulb be inserted repeatedly. Such a repetitive application frequently results in a "packing" or physical forcing of the collected mucus farther up into the nasal cavity or passage.

Accordingly, because of the ineffectiveness and overall inefficiency of known procedures and techniques, as generally described above, there is a need in this area of a more effective and efficient aspirator assembly. Such a proposed and improved assembly should be structured to facilitate the ability of parents, caregivers or other individuals to quickly and effectively remove collected fluid from the nasal passage in order to allow proper breathing by the afflicted individual. In an attempt to overcome problems set forth above, mechanical devices have been devised which attempt to overcome the disadvantages and problems of the manually operable squeeze bulb structure. However, while such prior attempts may have been considered at least minimally operative, many known devices still do not quickly and efficiently remove the collected fluid from the blocked nasal cavity in an effective manner.

Therefore, there still exists a need in this area for an aspirator assembly which is capable of being used on infants, small children as well as adult individuals. Such proposed assemblies should be capable of use without necessitating the discomfort of the individual being aspirated. Further, an improved and proposed aspirator assembly should be capable of being hand held, at least partially self contained and dimensioned and structured to assure proper operation and effective aspiration of the individual.

SUMMARY OF THE INVENTION

This invention is directed to an aspirating assembly dimensioned and configured to be hand held and operative by a single hand of a user and functional to aspirate the nasal cavity of an individual including, but not limited to, infants and children. The assembly is self contained at least to the extent of including a battery operated vacuum pump or other negative pressure source disposed within a casing. A cover is removably attached to the casing and at least partially defines a receiving chamber into which aspirated fluid from the nasal cavity is received. In addition, a collection container is removably disposed within the receiving chamber in receiving relation to a predetermined portion of the aspirated fluid, which is at least partially defined by the heavier material mucus and other substances. For purposes of clarity, the term "aspirated fluid" is herein meant to include a lighter, gaseous phase such as, but not necessarily limited to, air which is removed from the nasal cavity during the aspirating procedure. In addition, "aspirated fluid" is also meant to include a "heavier" material phase, generically described herein as mucus. Accordingly, the aspirated mucus is accurately referred to herein as a "predetermined portion" of the aspirated fluid as described in greater detail hereinafter.

The aspirator assembly further includes an inlet assembly connected to or formed as part of the removable cover. The inlet assembly is structured to further facilitate the direction of flow of the heavier, predetermined portion of the aspirated fluid into the collection container. Thereafter, the container and collected mucus portion of the aspirated fluid are collectively disposed of after the aspiration procedure has been completed. Accordingly, the contamination and possible reduction of health hazards are accomplished by allowing for the disposal and replacement of the collection container as versus its cleaning, after use.

As will be explained in greater detail hereinafter, the negative pressure source and its power supply in the form of a battery pack are housed within a hollow interior of the casing and are respectively configured and dimensioned to facilitate the casing being held and operated by a single hand of a user or operator. As such, the vacuum or negative pressure created by the negative pressure source communicates with the receiving chamber and with the aforementioned inlet assembly. Upon the creation of a sufficient negative pressure, the direct application of the inlet assembly into an appropriate portion of the nasal cavity, will serve to remove the trapped and/or collected aspirated fluid. As set forth above and more fully explained hereinafter, the cooperative disposition and structuring of the inlet assembly in aligned relation with the interior of the collection container facilitates the collection of the heavier mucus or predetermined portion of the aspirated fluid into the interior of the container.

Concurrently as both air and mucus, collectively and at least partially defining the aspirated fluid, are drawn into the receiving chamber through the aforementioned inlet assembly, the air, or gaseous portion of the aspirated fluid, will be effectively separated from the mucus and directed at least partially away from the interior of the collection container. Moreover, the gaseous portion of the aspirated fluid will be directed out from the interior of the receiving chamber and along a predetermined "path of fluid flow". Accordingly, the aforementioned path of fluid flow is also disposed and structured to establish fluid communication between the receiving chamber and the inlet assembly and the negative pressure source. As a result, at least a partial vacuum will develop within the interior of the receiving chamber and be maintained during the operation of the vacuum pump or other negative pressure source. Further, the disposition and overall structure of the path of fluid flow is such as to facilitate the passage of air and/or the lighter, gaseous phase of the aspirated fluid out from the interior of the receiving chamber, while restricting the passage of the predetermined, heavier portion of the aspirated fluid along the path of the fluid flow. As a result, the predetermined heavier portion of the aspirated fluid will be collected within the container for the collective disposal of the container and the collected mucus after completion of the aspiration procedure.

Other structural and operative features of the aspirating assembly include operative controls easily activated by one or more fingers of the user and a display, facilitating visualization of the various operative features and performance characteristics of the aspirating assembly during its activation, operation and overall use. Yet additional operative features and components of the aspirating assembly may include a sound generating assembly structured to produce music or other appropriate sounds, which may be especially appealing and therefore serve as a diversion to infants and children, during the aspirating procedure.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 6 is an exterior view of the cover represented in FIGS. 4 and 5.

FIG. 7 is an exterior view of a nozzle assembly as represented in FIGS. 1-3.

FIG. 8 is an exterior view of the disposable collection container as represented in FIGS. 4 and 5.

Like reference numerals refer to like parts throughout the several views of the drawings.

DETAILED DESCRIPTION OF THE PREFERRED EMBODIMENT

Figure 3:
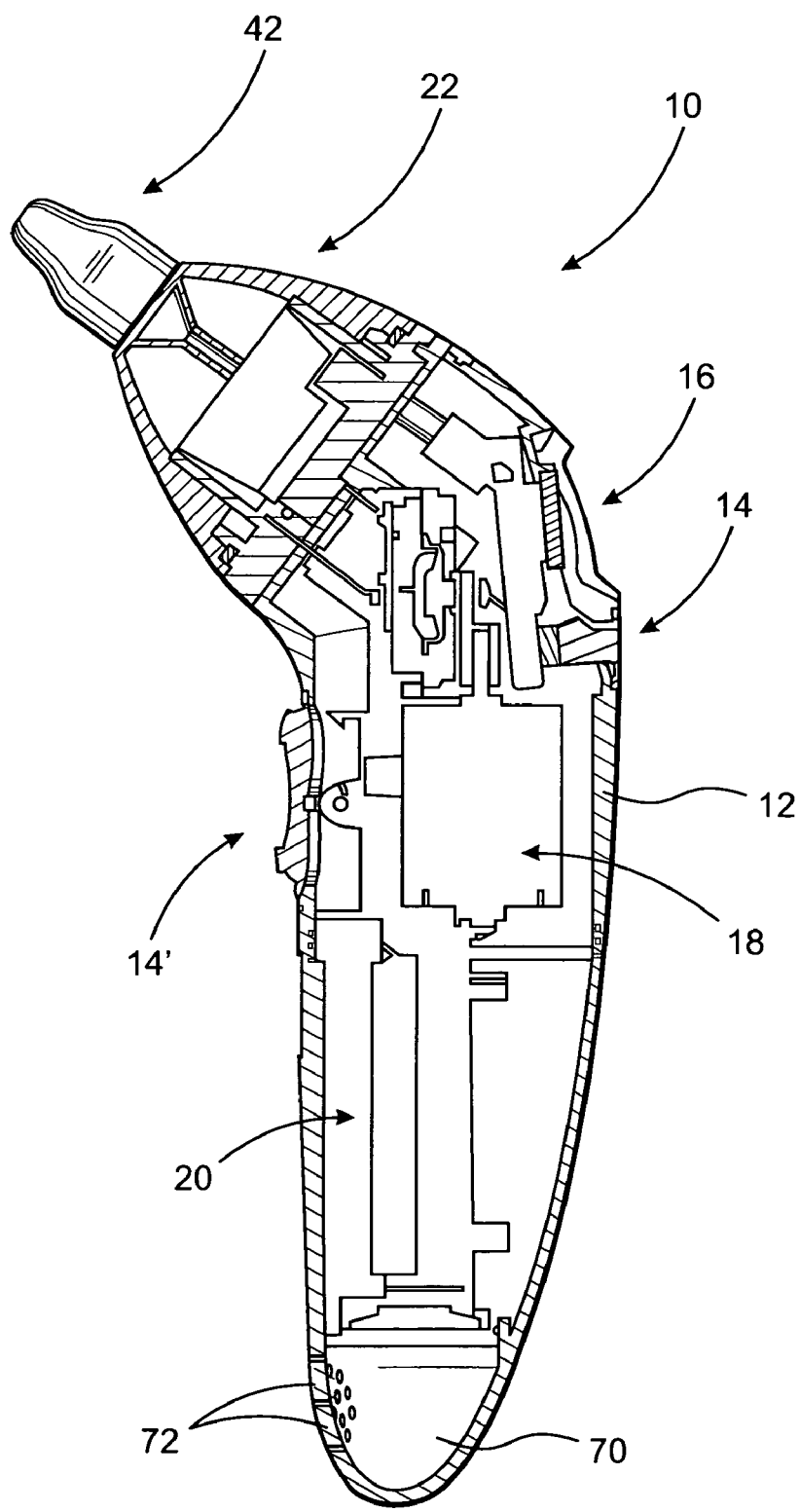
FIG. 3 is an interior view of the embodiment of FIGS. 1 and 2 representing various operative components contained within a handheld casing.

As shown in the accompanying Figures, the present invention is directed to an aspirator assembly generally indicated as 10 including an at least partially hollow interior casing 12, as represented in FIG. 3. The casing 12 is dimensioned and configured to be hand held and includes a plurality of operator buttons or like control members generally indicated as 14. The controls 14 facilitate activation and operation of the aspirator assembly 10 by a single hand of an operator. In conjunction therewith, a display assembly generally indicated as 16 is disposed in a readily observable location on the casing 12 and is cooperatively structured with appropriate control and operating circuitry (not shown) to allow visualization of the operational and performance characteristics of the aspirator assembly 10. Additional activation controls 14' may also be disposed on the casing 12 and generally, but not exclusively, may be operatively connected to appropriate control circuitry to serve as an on/off or other switch for the aspirator assembly 10.

Additional operative components of the aspirator assembly 10, include a negative pressure source, generally indicated as 18, which may include a vacuum pump or other appropriate structure. As such, the negative pressure source 18 is powered by a battery pack or battery assembly generally indicated as 20, which is also contained in a hollow interior portion of the casing 12. As set forth above, appropriate control and activating buttons 14 and 14' are electrically connected to provide control circuitry so as to activate and regulate operation of the aspirator assembly.

Figure 4:
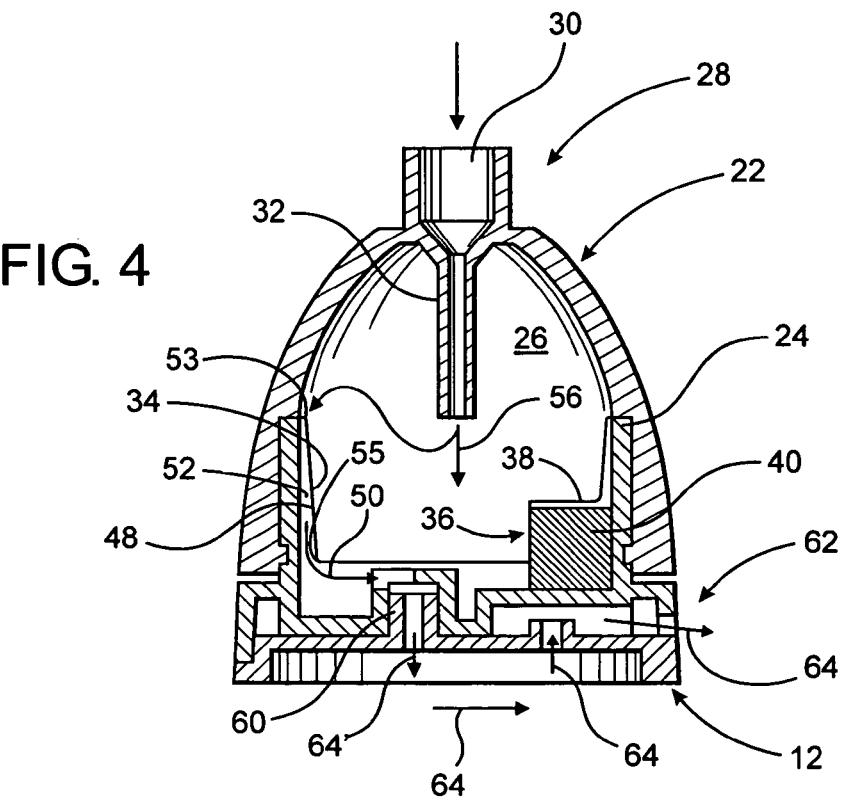
FIG. 4 is a sectional view of the interior of a receiving chamber as well as cooperative components including a cover and disposable collection container.
Figure 5:
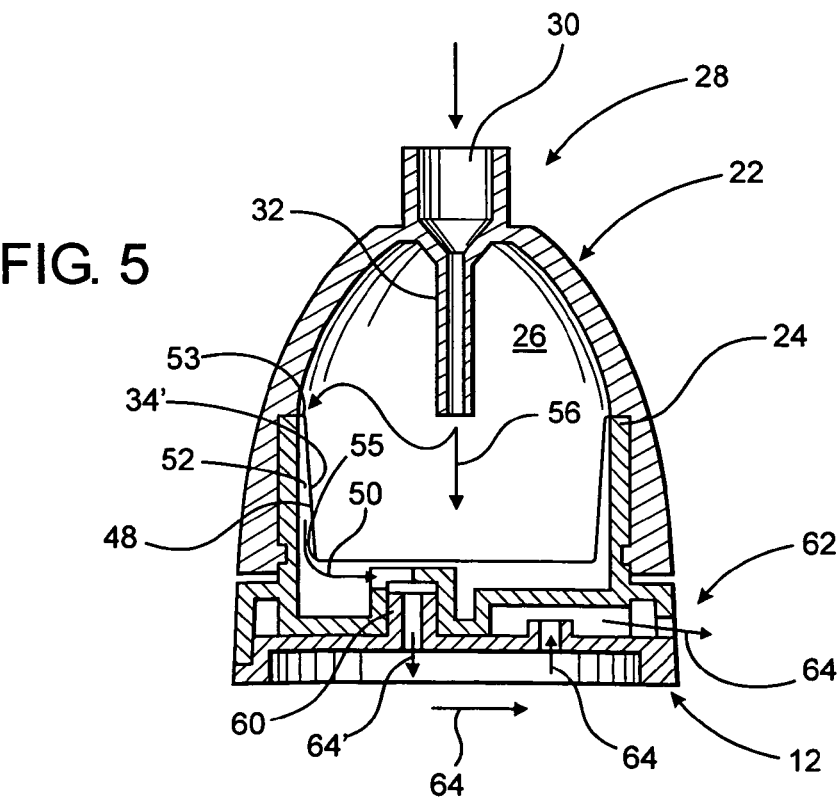
FIG. 5 is a sectional view similar to but structurally distinguishable from the embodiment of FIG. 4.

Yet additional operative components and features of the aspirator assembly 10 include a cover generally indicated as 22, which is shown in detail in FIG. 6 and schematically represented in FIGS. 4 and 5. The cover 22 is removably connected to the casing 12 so as to be readily detached therefrom for reasons to be explained in greater detail hereinafter. As such, the cover 22 is disposed in surrounding and at least partially interconnecting relation to a base portion 24 of the casing in the manner schematically represented in FIGS. 4 and 5. Accordingly, the cover 22, when disposed in its intended, connected position relative to the casing 12, at least partially defines a receiving chamber 26. In addition, an inlet assembly generally indicated as 28 is formed on or otherwise connected to the cover 22 and includes an inlet opening 30 and preferably an elongated conduit 32 extending into the interior of the receiving chamber 26.

Additional features of the aspirator assembly 10, specifically relating to the receiving chamber 26 and the receipt and collection of predetermined portions of the aspirated fluid is the provision of a collection container 34. The collection container 34 is made from a disposable material and is removably placed within the receiving chamber 26, on the interior of the cover 22. More specifically, the container 34 is removably disposed in a predetermined, operative orientation which facilitates the predetermined, heavier portion of the aspirated fluid being collected on the interior thereof. In the embodiment of FIG. 4, the disposable collection container 34 is additionally structured to at least partially include a portion of a stabilizing assembly generally indicated as 36. The portion of the stabilizing assembly 36 associated with the disposable collection container 34 may include some type of indentation, recess or other appropriate structure 38. Recess 38 is dimensioned, configured and disposed to be positioned in aligned registry with a step or other protruding structure portion 40 connected to or formed as part of the casing 12. As such, the recess 38 and the step 40 are cooperatively dimensioned and configured to come into aligned registry and/or confronting engagement with one another when the container 34 is in a preferred, operative orientation. This preferred, operative orientation facilitates the collection of the heavier aspirated fluid therein by assuring that the container 34 is properly positioned relative to the inlet assembly 28 and in particular the elongated conduit 32.

Accordingly, in at least one preferred embodiment, the stabilizing assembly 36 comprises both the first portion 38 formed in or as part of the collection container 34 and the additional second portion 40 mounted on or connected to the casing 12. However, as demonstrated in FIGS. 5 and 8, the collection container 34' may be absent the first recessed portion 38 which at least partially defines the stabilizing assembly 36. Similarly, the second portion 40 may be completely absent from the casing 12 so as to define yet another preferred embodiment of the aspirator assembly 10 of the present invention.

Yet another structural component associated with the preferred embodiment of the aspirator assembly 10 includes a nozzle or like introductory member generally indicated as 42. The nozzle 42 is designed to be removably connected about the mouth or protruding portion 28' of the inlet assembly 28. In addition, the nozzle 42 comprises a hollow interior passage 44. The passage 44 terminates in oppositely disposed open ends 45 and 45' and as such is structured to facilitate passage of aspirated fluid from the nasal cavity in which the nozzle 42 is at least partially placed. Proper positioning of the nozzle 42 within a nasal passage is further facilitated by a substantially diverging configuration as the nozzle extends from the outer open end 45 to the inner open end 45'. The diverging configuration of nozzle 42 further facilitates its removable connection to the exterior, outwardly extending mouth 28' of the inlet assembly 28, as set forth above. It should be further noted that the nozzle 42, as well as the other cooperative components of the aspirator assembly 10 may be structured to aspirate fluid from the nasal cavity of adult individuals as well as infants and children, wherein the size of the nozzle may vary accordingly.

Intended, proper operation of the aspirator assembly 10 is predicated on the establishment of fluid communication between the negative pressure source 18, the receiving chamber 26, the inlet assembly 28 and the nasal cavity of an individual. In turn communication of sufficient negative pressure with the nasal cavity necessitates the placement of the nozzle 42 at least partially therein. More specifically, the receiving chamber 26 is disposed in fluid communication with the negative pressure source 18 by virtue of a path of fluid flow extending therebetween. Accordingly, as represented in FIG. 8, one preferred embodiment of the present invention includes the collection container 34 and/or 34' having an exterior wall surface generally indicated as 48, extending continuously along an outermost periphery of collection container 34 and 34', in surrounding relation to a hollow interior of the container 34 and 34'. As also represented in FIG. 8 and described in greater detail hereinafter, the exterior wall surface 48 is structured to at least partially define the aforementioned path of fluid flow between the negative pressure source 18 and the interior of the receiving chamber 26. Such path of fluid flow at least partially extends along the exterior surface 48 and/or more specifically, the exterior wall surface 48 as schematically indicated by directional arrow 50 in FIGS. 4 and 5. More specifically, the container 34 and 34' includes an opening 49 and the hollow interior disposed in communicating relation with the interior of the receiving chamber 26 for receipt and collection of the mucous portion of the aspirated fluid therein. A closed end 49' of the container 34 and 34' is oppositely disposed to the opening 49.

Therefore, the path of fluid flow 50 is even more specifically defined by one or more channels 52 formed in the exterior surface 48, wherein the channels 52 comprise elongated recesses or indented portions having oppositely disposed open ends 53 and 55. Therefore, as schematically represented in FIG. 8, a first of the open ends 53 is disposed adjacent the opening 49 and a second of the open ends 55 is disposed exteriorly of the hollow interior of the container 34 and/or 34' and adjacent the closed end 49'. The presence of at least one or preferably a plurality of channels 52 in the exterior surface 48 of the collection container 34, 34' allows a gaseous portion of the aspirated fluid entering the chamber 26 to pass directly into a correspondingly disposed open end 53 of the channel 52. This directed passage of the gaseous portion of the aspirated fluid is due to the presence of negative pressure along the predetermined flow path 50 which in turn is based on fluid communication between the negative pressure source 18 and the interior of the receiving chamber 26. However, the dimension, disposition and overall structure of the one or more channels 52 and in particular open end 53 of the one or more channels 52 is such as to restrict a predetermined heavier or mucus portion of the aspirated fluid from entering into the flow path 50 and/or passing through the open end 53.

More specifically, aspirated fluid removed from the nasal cavity of an individual will comprise both mucus, representing a more dense or "heavier" portion of the aspirated fluid, as well as a gaseous, lighter portion of the aspirated fluid. Accordingly, the disposition and configuration of the inlet assembly 28 specially, but not exclusively, including the elongated conduit 32 being in at least partial alignment or registry with the interior of the collection container 34, 34' results in a predetermined portion of the aspirated fluid, specifically including the heavier mucus portion, being delivered directly into the collection container 34 as schematically indicated by directional arrow 56. In contrast, the lighter or gaseous phase of the aspirated fluid will be directed, under the influence of the created negative pressure, through the open end 53 of the one or more channels 52 which at least partially define the path of fluid flow. As set forth above, the dimension and disposition of the open end 53, of the one or more channels 52, is such as to restrict passage of the heavier phase or mucus portion of the aspirated fluid, into the channel(s) 52 and along the flow path 50.

With further reference to the embodiments of FIGS. 4 and 5, upon the gaseous phase of the aspirated fluid passing along the one or more channels 52, at least partially defining the predetermined path of fluid flow 50, it will continue to pass through appropriate seals and/or valves, as schematically represented as 60, and eventually exit through a venting assembly 62 as schematically represented by sequential directional arrows 64. As also represented in FIGS. 4 and 5, fluid communication between the negative pressure source 18 and the receiving chamber 26 is established by a fluid flow connection 64' communicating with both the path of fluid flow 50 and the negative pressure source 18.

Yet another feature of at least one preferred embodiment of the present invention is represented in FIG. 3. More specifically, a sound generating assembly generally indicated as 70 may also be housed on the interior of the casing 12 and be powered by the battery or other appropriate and preferably self contained power supply 20. As such, the sound generating assembly 70 may be structured to produce music or other appropriate sounds which would be especially attractive to infants and smaller children. As such, activation of the controls 14 and/or 14' would affect operation of the sound generating assembly 70 such that music or other appropriate sound could be produced concurrently to the aspirating procedure. Such sound production would have the effect of pleasing infants or small children and/or distracting them from the aspirating procedure and/or any discomfort associated therewith. Upon activation or operation, the sound generating assembly 70 will produce and/or direct sound outwardly from the casing as through appropriate apertures or openings 72 in the casing and/or in the sound generating assembly itself.

Figures 1, 2:
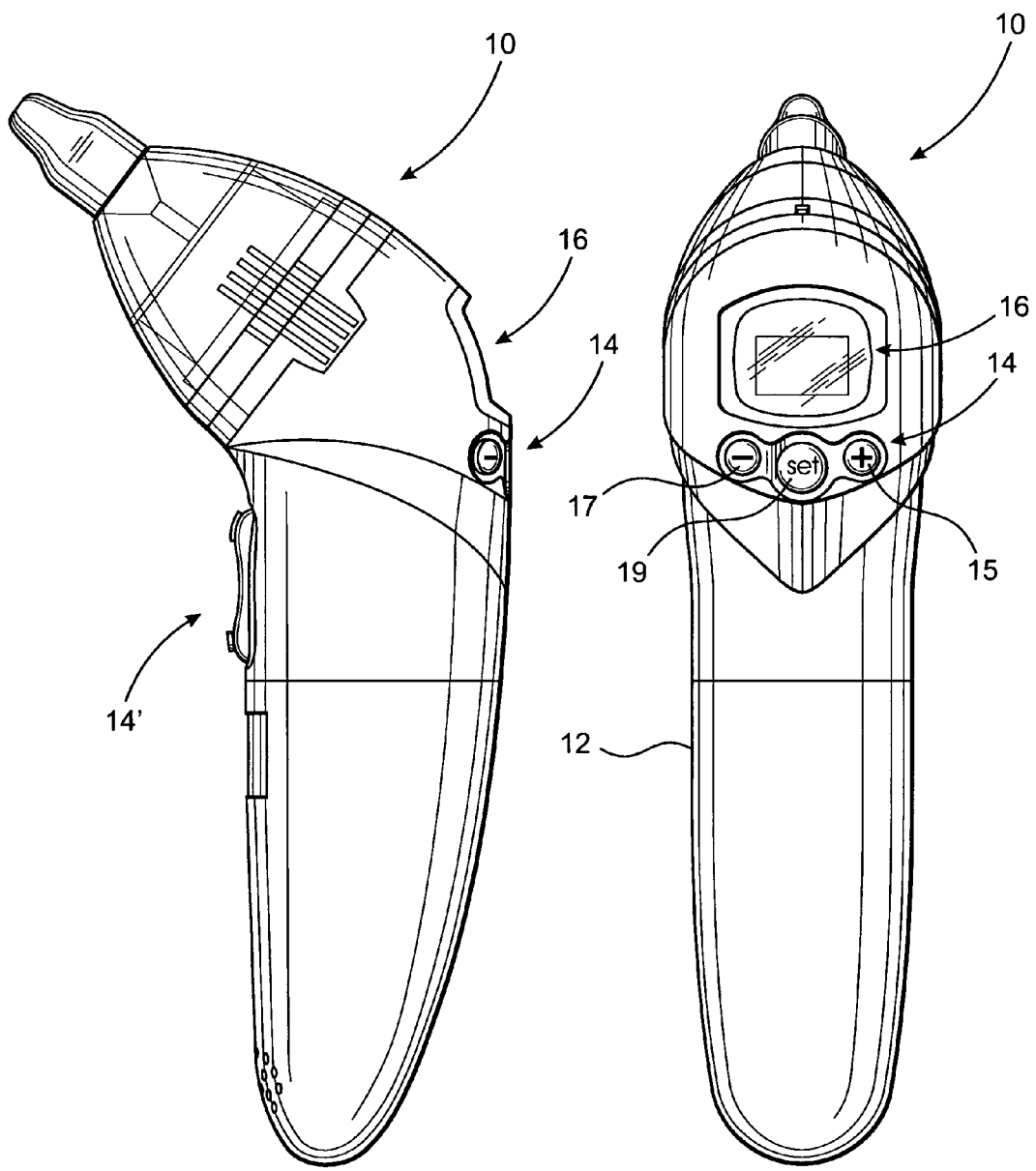
FIG. 1 is a side view of the aspirating assembly of the present invention.
FIG. 2 is a front view of the embodiment of FIG. 1.

Yet another feature of the present invention is best described with primary reference to FIG. 2. As represented therein, the control assembly 14 includes a plurality of operating or control buttons which may be further defined by "plus" and "minus" buttons or control member 15 and 17 respectively. These plus and minus buttons 15 and 17 may be used in combination with a "set" button 19, to the extent that negative pressure created by the negative pressure source 18 may be increased or decreased dependent, at least in part, on the amount of suction necessary to remove the blocked mucus and/or other fluid from within the nasal cavity or passage. Once the appropriate degree of negative pressure has been determined, the set button 19 may be utilized to maintain the negative pressure at the determined value.

As should be apparent, care is taken to only use the amount of negative pressure required to remove such blockage, especially when the aspirating procedure, using the aspirating assembly 10 is performed on a small infant and/or child. As such, the controls 14 are selectively operable to effectively and accurately regulate the degree of negative pressure or suction applied to the nasal cavity or passage. In addition, the visual display 16 may be easily viewed so as to provide the operator with an indication of the degree of suction or negative pressure applied to the nasal cavity or passage of the individual being aspirated.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. An assembly structured to aspirate a nasal cavity, said assembly comprising:
   a casing including an at least partially hollow interior,
   a cover structured to at least partially define a receiving chamber on an interior thereof when said cover is connected to said casing,
   a negative pressure source disposed within said casing in fluid communication with said receiving chamber,
   an inlet assembly disposed in communicating relation with said receiving chamber and structured to direct aspirated fluid into said receiving chamber,
   a collection container removably disposed within said receiving chamber and including an opening, a hollow interior and a closed end oppositely disposed to said opening,
   said hollow interior disposed in communicating relation with said receiving chamber and in receiving, retaining relation to a heavier phase of the aspirated fluid,
   said collection container further including an exterior wall surface extending continuously about and at least partially defining an outermost periphery of said collection container in surrounding relation to said hollow interior,
   a path of fluid flow for a lighter phase of the aspirated fluid from said receiving chamber to an exterior thereof, and
   said path of fluid flow at least partially defined by a channel assembly including at least one elongated channel integrally recessed into said exterior wall surface of said collection container, said one elongated channel extending between and terminating at said opening and said closed end.

2. An assembly as recited in claim 1 comprising a nozzle connected to said inlet assembly and dimensioned and configured to at least partially enter into the nasal cavity.

3. An assembly as recited in claim 2 wherein said inlet assembly is formed in said cover and structured to be removably connected to said nozzle; said nozzle disposed and structured to direct aspirated fluid from the nasal cavity to said inlet assembly.

4. An assembly as recited in claim 1 wherein said inlet assembly comprises an elongated conduit disposed in substantially aligned communicating relation with an interior of said collection container.

5. An assembly as recited in claim 4 wherein said inlet assembly comprises an inlet opening disposed in communicating relation with said elongated conduit and cooperatively structured to direct the aspirated fluid into said receiving chamber.

6. An assembly as recited in claim 1 wherein said inlet assembly further comprises an inlet opening and an elongated conduit portion connected to said inlet opening and disposed to direct at least a predetermined portion of the aspirated fluid into said collection container.

7. An assembly as recited in claim 6 wherein said receiving chamber is structured to direct at least a portion of the aspirated fluid exteriorly of said collection container and out of said receiving chamber.

8. An assembly as recited in claim 1 wherein said collection container is disposable and removably positioned within said receiving chamber, said collection container formed of a material which facilitates disposal thereof with collected aspirated fluid therein, after completion of an aspirating procedure.

9. An assembly as recited in claim 1 wherein said one elongated channel comprises oppositely disposed open ends, a first of said open ends disposed in adjacent relation to said opening of said collection container and a second of said open ends disposed adjacent said closed end of said collection container.

10. An assembly as recited in claim 9 wherein said first of said open ends is disposed in communicating relation with aspirated fluid received within said receiving chamber, said first open end dimensioned to facilitate passage of the lighter phase of the aspirated fluid there through and restrict passage of the heavier phase of the aspirated fluid from passing there through.

11. An assembly as recited in claim 1 further comprising a stabilizing assembly including a recess formed on said closed end of said collection container and a protruding structure formed on said casing, said protruding structure and said recess disposed in aligned registry with one another to define placement of said collection container in a predetermined operative orientation within said receiving chamber.

12. An assembly structured to aspirate a fluid from a nasal cavity;

a casing including a negative pressure source disposed thereon, a cover removably connected to said casing structured to at least partially define a receiving chamber on an interior thereof, a collection container removably disposed in a predetermined operative position within said receiving chamber, said collection chamber including an opening, a hollow interior and a closed end oppositely disposed to said opening, an inlet assembly disposed in communicating relation with said receiving chamber and structured to direct aspirated fluid into said receiving chamber, said hollow interior of said collection container disposed in communicating relation with said receiving chamber and in receiving, retaining relation to a heavier phase of the aspirated fluid, said collection container further including an exterior wall surface extending continuously about and at least partially defining an outermost periphery of said collection container in surrounding relation to said hollow interior, a path of fluid flow for a lighter phase of the aspirated fluid extending from the interior of said receiving chamber to an exterior of said receiving chamber, said path of fluid flow at least partially defined by a channel assembly including a plurality of elongated channels integrally recessed into said exterior wall surface of said collection container in spaced relation to one another about said outermost periphery, each of said plurality of channels extending between and terminating at said opening and said closed end, each of said plurality of channels comprising oppositely disposed open ends, a first of said open ends of each channel disposed in adjacent relation to said opening and a second of said open ends of each channel disposed adjacent said closed end, and said first of said open ends of each of said plurality of channels being disposed in communicating relation with aspirated fluid received within said receiving chamber, each of said first open ends dimensioned to facilitate the lighter phase of the aspirated fluid there through and restrict passage of the heavier phase of the aspirated fluid from passing there through.

13. An assembly as recited in claim 12 wherein said inlet assembly and said collection container are cooperatively disposed and structured to direct the heavier phase of the aspirated fluid into said collection container.

14. An assembly as recited in claim 12 wherein said inlet assembly comprises an elongated conduit disposed in substantially aligned, communicating relation with an interior of said collection container, said inlet assembly further comprising an inlet opening disposed and structured to direct aspirated fluid into said elongated conduit.

15. An assembly as recited in claim 12 further comprising a stabilizing assembly at least partially formed on said collection container, said stabilizing assembly disposed and structured to facilitate placement of said collection container in a predetermined operative orientation within said receiving chamber.

16. An assembly as recited in claim 15 wherein said stabilizing assembly is at least partially disposed in said casing, said predetermined operative orientation at least partially defined by alignment of corresponding portions of said stabilizing assembly formed on said collection container and disposed on said casing.

17. An assembly as recited in claim 12 wherein said collection container is formed of a disposable material and disposable from said receiving chamber and said casing, with the retained heavier phase of the aspirated fluid therein.

* * * * *